US012066386B2

United States Patent
Chen et al.

(10) Patent No.: US 12,066,386 B2
(45) Date of Patent: Aug. 20, 2024

(54) SAMPLING DEVICE, SEMI-AUTOMATIC SAMPLE FEEDING DEVICE AND TEST PAPER DETECTION SYSTEM

(71) Applicant: National Taiwan University, Taipei (TW)

(72) Inventors: Chien-Fu Chen, Taipei (TW); Shih-Jie Chen, Taipei (TW); Jia-Hui Lin, Taipei (TW)

(73) Assignee: National Taiwan University, Taipei (TW)

( * ) Notice: Subject to any disclaimer, the term of this patent is extended or adjusted under 35 U.S.C. 154(b) by 358 days.

(21) Appl. No.: 17/318,605

(22) Filed: May 12, 2021

(65) Prior Publication Data

US 2022/0304665 A1 Sep. 29, 2022

(30) Foreign Application Priority Data

Mar. 25, 2021 (TW) .................................. 110110872

(51) Int. Cl.
*G01N 1/14* (2006.01)
*G01N 21/78* (2006.01)
(Continued)

(52) U.S. Cl.
CPC ........... *G01N 21/8483* (2013.01); *G01N 1/14* (2013.01); *G01N 21/78* (2013.01);
(Continued)

(58) Field of Classification Search
CPC ...... G01N 21/8483; G01N 1/14; G01N 21/78; G01N 2001/1427; G01N 2021/7786;
(Continued)

(56) References Cited

U.S. PATENT DOCUMENTS 4,750,373 A * 6/1988 Shapiro ................. B01L 3/0234
73/864.18

FOREIGN PATENT DOCUMENTS

CN 204072977 U * 1/2015

OTHER PUBLICATIONS

Chen, Chien-Fu, "Infectious Disease Diagnosis and Water Quality Monitoring Using Nanomaterials Immobilized Paper and a Flow Controllable Microfluidic Device," Taiwan Innotech Exposition, Taipei, Taiwan, R.O.C., Sep. 24-26, 2020, p. 32. p. 30.

* cited by examiner

*Primary Examiner* — Robert R Raevis
(74) *Attorney, Agent, or Firm* — Amin, Turocy & Watson, LLP

(57) ABSTRACT

A sampling device is provided, including: a syringe barrel having an opening and a holding portion; a plunger body having a protruding wall and disposed in the syringe barrel through the opening, where the protruding wall has a first recessed portion; a spring disposed around the plunger body; and a fastening assembly having an engaging structure for engaging the fastening assembly with the holding portion, a groove rail for receiving the protruding wall of the plunger body and a fastening portion for limiting displacement of the plunger body. A semi-automatic sample feeding device is further provided and includes the sampling device and a flow control device, and a test paper detection system is also provided and includes the semi-automatic sample feeding device and a test paper device. The test paper detection system is able to stably introduce samples, suitable for large-volume samples, which meets the needs of point-of-care applications.

19 Claims, 8 Drawing Sheets

(51) Int. Cl.
  *G01N 21/84* (2006.01)
  *A61B 10/02* (2006.01)
  *G01N 21/77* (2006.01)
(52) U.S. Cl.
  CPC ................ *A61B 2010/0208* (2013.01); *G01N 2001/1427* (2013.01); *G01N 2021/7786* (2013.01)
(58) Field of Classification Search
  CPC .... G01N 2001/1418; G01N 2001/1436; A61B 2010/0208; A61B 10/02
  USPC ... 73/64.56, 864.13, 864.18, 864.21, 864.73, 73/864.74; 422/501, 521
  See application file for complete search history.

SAMPLING DEVICE, SEMI-AUTOMATIC SAMPLE FEEDING DEVICE AND TEST PAPER DETECTION SYSTEM

CROSS-REFERENCE TO RELATED APPLICATION

This application claims the benefit of and priority to TW Application No. 110110872, filed Mar. 25, 2021, the contents of which are incorporated herein in their entirety.

BACKGROUND

1. Technical Field

The present disclosure relates to a sampling device and a semi-automatic sample feeding device having a sampling device and a flow control device, and more particularly, to a test paper detection system having a sampling device, a flow control device and a test paper device.

2. Description of Related Art

Conventionally, samples need to be sent to medical units or inspection centers for disease screening and environmental testing. Professional operators perform complicated processing steps and use sophisticated instruments for sample analysis. The sophisticated instruments are usually expensive and require additional energy for operation. Therefore, remote or resource-limited areas may not be able to afford the cost of the instruments and energy. Further, such a process is time-consuming and the test result cannot be obtained immediately. Furthermore, the professional operators must have relevant technical backgrounds and need to be pre-trained. As such, the human resources are insufficient and the amount of test is limited.

In order to rapidly control the spread of diseases in areas lack of medical resources, the global world is actively developing precision medicine, including point-of-care (POC). The system is used for detection and should meet the World Health Organization (WHO) requirements of affordability, sensitivity, specificity, stability, simple operation, rapidity, no large device, and portability.

Currently, a lot of POC testing devices such as test paper devices have been provided. However, they are only applicable to a sample volume of less than 200 μL, and if the sample concentration is too low, it is difficult to perform test paper screening. On the other hand, it is not easy to manually operate a large-volume sample and an electric pump is needed.

Therefore, there is a need to provide a test paper detection system that eliminates the need of an electric pump, is capable of stably feeding samples and suitable for large-volume sample POC.

SUMMARY

The present disclosure provides a sampling device, which comprises: a syringe barrel having an injection hole and an opening opposite to one another and a holding portion formed at an outer edge of the opening; a plunger body axially disposed in the syringe barrel through the opening, wherein a protruding wall is formed in an axial direction of the plunger body and a first recessed portion is formed in an extending direction of the protruding wall; a spring disposed around the plunger body; and a fastening assembly having a through hole allowing the plunger body to penetrate therethrough and an engaging structure communicating with the through hole, wherein the fastening assembly is engaged with the holding portion through the engaging structure, and a groove rail is formed on a wall of the through hole for receiving the protruding wall of the plunger body and a fastening portion is formed on the wall of the through hole for limiting a displacement of the plunger body.

In an embodiment, when the protruding wall moves along the axial direction of the syringe barrel in the groove rail such that the plunger body gradually moves away from the syringe barrel, the spring is compressed synchronously.

In an embodiment, in the axial direction of the plunger body, a length of the first recessed portion is greater than or equal to a length of the groove rail.

In an embodiment, the fastening portion is a receiving space in communication with the through hole such that when the first recessed portion of the plunger body enters the groove rail, the plunger body is rotated to allow the protruding wall to be received in the receiving space.

In an embodiment, the receiving space is a slot adjacent to the through hole.

In an embodiment, the slot has a closed end and the protruding wall abuts against the closed end, thereby limiting the displacement of the plunger body.

In an embodiment, the plunger body further has a stop member for limiting the spring between the stop member and the fastening assembly.

In an embodiment, the protruding wall further has a second recessed portion for the stop member to be engageably disposed in the second recessed portion of the plunger body.

In an embodiment, the plunger body has a piston at a front end thereof.

The present disclosure further provides a semi-automatic sample feeding device, which comprises the above-described sampling device and a flow control device connected to the injection hole of the sampling device.

In an embodiment, the sampling device automatically sends a sample to the flow control device via the spring.

In an embodiment, the flow control device comprises a top member, a film and a bottom member, wherein the top member and the bottom member are joined together with a film receiving space formed therebetween for receiving the film.

In an embodiment, the top member has an inflow channel and the bottom member has a discharge channel, and the injection hole of the syringe barrel communicates with the inflow channel of the top member.

In an embodiment, a front end of the syringe barrel with the injection hole is inserted into the inflow channel of the top member.

In an embodiment, the inflow channel and the discharge channel communicate with the film receiving space in an unaligned manner.

In an embodiment, the film receiving space is formed in the bottom member for receiving the film.

In an embodiment, the film has a through hole.

In an embodiment, the film is made of a polysiloxane polymer.

In an embodiment, the film has a thickness between 1.2 mm and 2.2 mm.

The present disclosure further provides a test paper detection system comprising the above-described semi-automatic sample feeding device and a test paper device connected to the discharge channel of the flow control device.

In an embodiment, the sampling device automatically sends a sample from the flow control device to the test paper device via the spring.

In an embodiment, the test paper device comprises a top assembly, a seal ring, a test paper and a bottom assembly, wherein the top assembly and the bottom assembly are joined together with the test paper sealed between the top assembly and the bottom assembly.

In an embodiment, the top assembly has an inflow channel and the bottom assembly has a discharge channel, and the discharge channel of the flow control device communicates with the inflow channel of the top assembly.

In an embodiment, the top assembly comprises a top housing and a top internal member disposed in the top housing, and the bottom assembly comprises a bottom housing and a bottom internal member disposed in the bottom housing.

In an embodiment, the test paper is a fluorescent or colorimetric test paper.

In an embodiment, a plurality of the test papers are provided in a stack manner.

According to the present disclosure, the protruding wall of the plunger of the sampling device can be correspondingly received in the groove rail of the fastening assembly and move along the groove rail. Further, the plunger can be rotated such that the protruding wall is separated from the groove rail and moved to the fastening portion of the fastening assembly. As such, the protruding wall and the fastening portion are joined together and hence the plunger is at a fixed position. Under such a mechanism, only by rotating the plunger after sampling, the sample can be kept in the syringe barrel without force application.

Secondly, after sampling, the sampling device can be connected to the test paper device, and the plunger is rotated again such that the protruding wall is separated from the fastening portion and moved back to the groove rail. At this point, the elastic restoring force of the spring will cause the plunger to push the sample automatically. Hence, the sample is fed from the syringe barrel to the subsequent devices such as the flow control device and test paper device, thereby achieving the purpose of semi-automation.

Thirdly, the elastic restoring force of the spring pushes the sample to the film in the flow control device so as to generate a back pressure capable of stably controlling the flow rate. Consequently, the sample can be fed to the test paper device at a constant flow rate, thus obtaining an excellent test paper detection system.

Fourthly, a variety of test papers can be used in the test paper device of the present disclosure and easily replaceable, and the test papers can be stacked to perform various detections on a single-fed sample.

Fifthly, the test paper detection system of the present disclosure dispenses with electric power, has a low cost, is lightweight, convenient to carry, and easy to operate, thus facilitating point-of-care testing.

Sixthly, the test paper detection system of the present disclosure is suitable for large-volume samples (e.g., greater than 200 μL or even greater than 1 mL) and has a wider application range compared with the conventional test paper detection device usually having an upper limit of 200 μL.

BRIEF DESCRIPTION OF THE DRAWINGS

FIGS. 3A-1, 3A-2, 3B-1 and 3B-2 are schematic perspective views of the sampling device at different states, wherein FIG. 3A-1 shows a state of the sampling device when no force is applied to the plunger body, FIG. 3A-2 shows relative configuration between the plunger body and the fastening assembly of FIG. 3A-1, FIG. 3B-1 shows a state of the sampling device when the plunger body is gradually pulled out of the syringe barrel and rotated by applying a force, and FIG. 3B-2 shows relative configuration between the plunger body and the fastening assembly of FIG. 3B-1.

DETAILED DESCRIPTION

Figure 1:
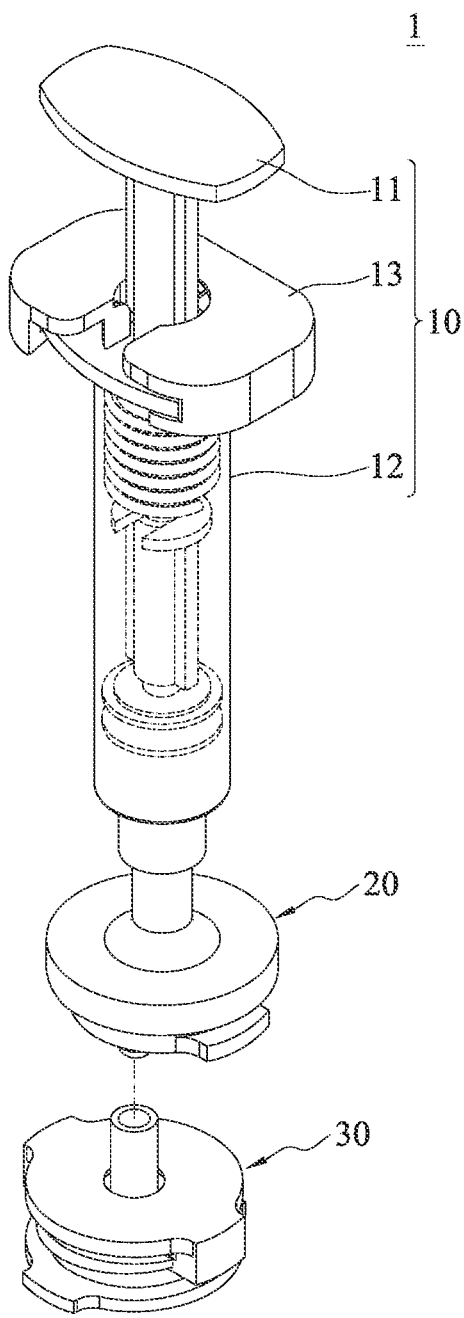
FIG. 1 is a schematic perspective view of a test paper detection system according to an embodiment of the present disclosure.

The following illustrative embodiments are provided to illustrate the present disclosure, these and other advantages and effects can be apparent to those skilled in the art after reading this specification.

It should be noted that all the drawings are not intended to limit the present disclosure. Various modifications and variations can be made without departing from the spirit of the present disclosure.

If a term "include," "comprise" or "have" specifies the presence of certain elements, unless otherwise indicated, it does not exclude other elements such as components, structures, areas, positions, devices, systems, steps or connections.

Further, terms such as "first," "second," "upper," "lower," "top," "bottom," "side," "front," "rear," etc., are merely for illustrative purposes and should not be construed to limit the scope of the present disclosure. Furthermore, singular forms "a," "an" and "the" are intended to include plural forms as well, unless the context clearly indicates otherwise. In addition, "or" and "and/or" are interchangeable in the specification.

Terms such as "engageably connect," "connect" and "engage" are intended to indicate that a plurality of elements are directly or indirectly joined together. "Direct joining" is intended to indicate that the plurality of elements are in direct contact and joined together. "Indirect joining" is intended to indicate that the plurality of elements are joined through at least a connecting element. The "joining" method includes, but not limited to, stitching, bonding, adhering, embedding, screwing, engaging, nailing, clamping, attaching, threading, mortising, placing, integral forming or a combination thereof.

A numerical range described herein is inclusive and can be combined. Any numerical value falling within the numerical range should be included in the scope of the present disclosure, and can also be used as a maximum or minimum value to derive a secondary range. For example, the numerical range of "1 cm to 5 cm" can be understood as including 1.5 cm, 2 cm and other values, and also including any secondary range between the minimum value of 1 cm and the maximum value of 5 cm, for example: 1 cm to 4 cm, 2 cm to 5 cm, etc.

A first aspect of the present disclosure is a sampling device, which has a syringe barrel, a plunger member and a fastening assembly. A spring is disposed around the plunger member.

In an embodiment, the syringe barrel has an injection hole and an opening opposite to one another, the plunger member is disposed in the syringe barrel through the opening, and the fastening assembly is disposed at the opening end of the syringe barrel. The plunger member can be in a fixed position by joining with the fastening assembly. More specifically, one end of the plunger member abuts against an end wall of the injection hole of the syringe barrel. When sampling with the sampling device, a force is applied to the plunger member so as to cause the plunger member to leave the end wall of the injection hole and a portion of the plunger member moves along an axial direction of the syringe barrel and gradually moves away from the syringe barrel. At the same time, the spring disposed around the plunger member is compressed. After sampling, the plunger member is fastened to the fastening assembly, and the sample is kept in the syringe barrel. Even if no force is applied, the sample will not leak through the injection hole. During a sample feeding process, the plunger member is not fastened by the fastening assembly, and due to an elastic restoring force of the spring, the plunger member is automatically pushed into the syringe barrel and hence the sample is pushed out through the injection hole. The sample feeding process is continued until the plunger member abuts against the end wall of the injection hole of the syringe barrel.

Figure 2:
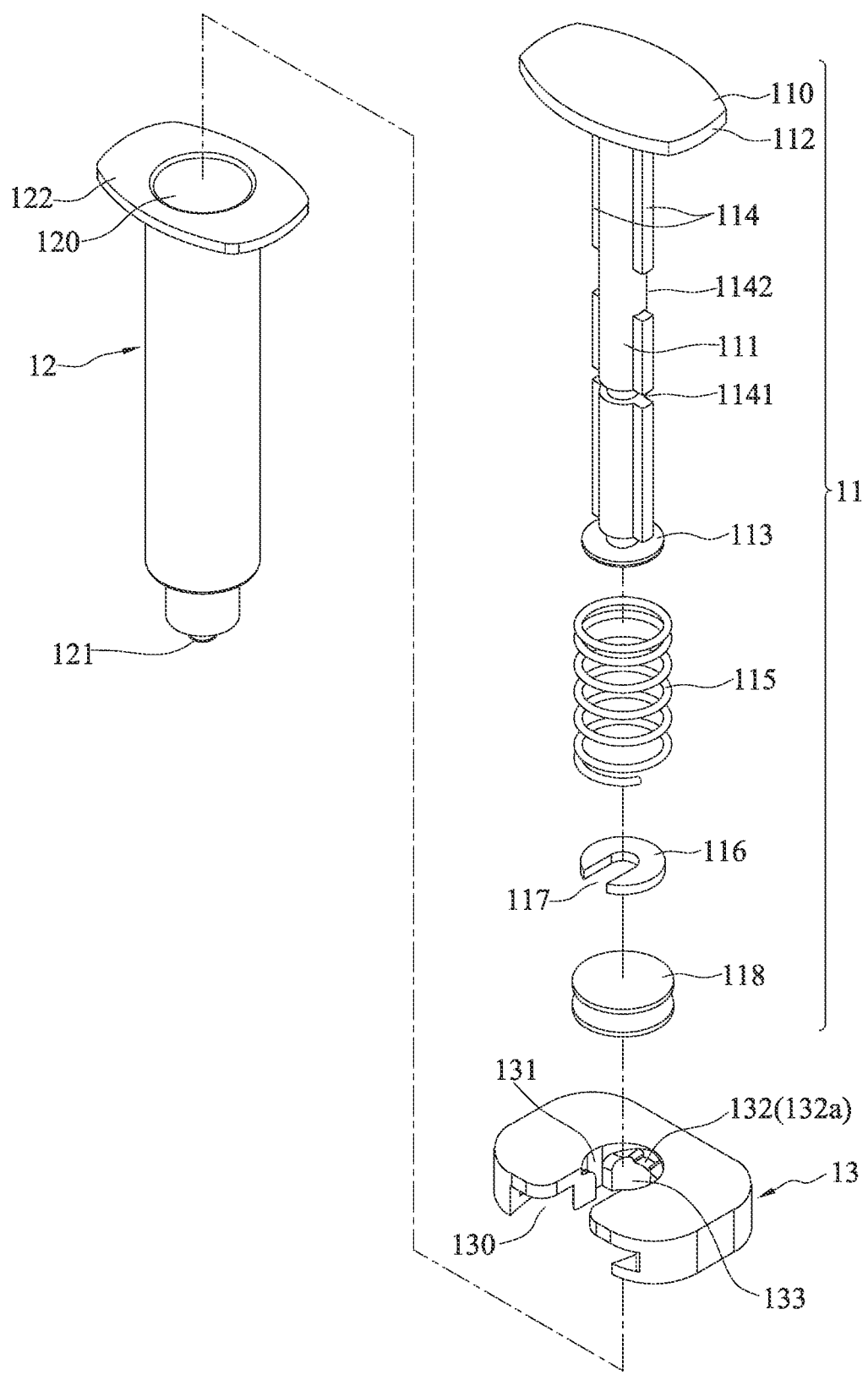
FIG. 2 is a schematic exploded view of a sampling device according to an embodiment of the present disclosure.

FIGS. 1 and 2 are schematic views of a sampling device according to an embodiment of the present disclosure. Referring to FIGS. 1 and 2, the sampling device 10 has a syringe barrel 12, a plunger member 11 and a fastening assembly 13.

The plunger member 11 includes a plunger 110, a spring 115 and a piston 118. The plunger 110 has a plunger body 111, an end plate 112, a joining portion 113 and a protruding wall 114. The protruding wall 114 has a first recessed portion 1142. The joining portion 113 is disposed at a bottom of the plunger body 111 and the end plate 112 is disposed at a top of the plunger body 111. The projection area of the end plate 112 is greater than the radial cross-sectional area of the plunger body 111 so as to facilitate application of a force on the end plate 112 for pulling the plunger member 11 during sampling. The spring 115 is disposed around the plunger body 111, the piston 118 is disposed at the bottom of the plunger body 111 and fastened to the joining portion 113, the protruding wall 114 is formed along an axial direction of the plunger body 111, and the first recesses portion 1142 is formed along an extension direction of the protruding wall 114.

The syringe barrel 12 has an injection hole 121 and an opening 120 opposite one another and a holding portion 122 formed at an outer edge of the opening 120. The plunger member 11 is disposed in the syringe barrel 12 through the opening 120. When no force is applied, one end of the plunger member 11 such as the piston 118 abuts against an end wall of the injection hole of the syringe barrel 12.

The fastening assembly 13 has an engaging structure 130, a groove rail 131, a fastening portion 132 and a through hole 133. The fastening assembly 13 is disposed on the holding portion 122 of the syringe barrel 12 through the engaging structure 130 so as to be joined with the syringe barrel 12. Referring to FIG. 2, the engaging structure 130 and the holding portion 122 can have a tenon-mortise structure. The engaging structure 130 is a mortise and the holding portion 122 is a corresponding tenon that can be inserted into the engaging structure 130. The through hole 133 corresponds to the opening 120 of the syringe barrel so as to allow the plunger body 111 to be inserted into the through hole 133. The groove rail 131 and the fastening portion 132 are formed on a wall of the through hole 133. The groove rail 131 matches and receives the protruding wall 114 of the plunger body 111 so as to allow the plunger body 111 to move through the matched protruding wall 114 and the groove rail 131. The fastening portion 132 can be a receiving space, such as a slot, in communication with the through hole 133 and used for limiting the displacement of the plunger body 111. The groove rail 131 and the fastening portion 132 are positioned in different radial directions of the through hole 133. In an embodiment, the groove rail 131 and the fastening portion 132 are spaced from one another by an angle of 90 degrees. In other embodiments, the spacing angle can be, but not limited to, greater than 0 to 180 degrees or greater than 0 to 90 degrees. For example, the spacing angle can be 10, 20, 22.5, 30, 40, 45, 50, 60, 67.5, 70, 75, 80, 90, 100, 110, 112.5, 120, 130, 135, 140, 150, 157.5, 160, 170, 180 degrees, etc.

Both ends of the groove rail 131 are open, and in the axial direction of the plunger body 111, the length of the first recessed portion 1142 of the protruding wall 114 is greater than or equal to that of the groove rail 131. Therefore, when the first recessed portion 1142 completely enters the groove rail 131, the protruding wall 114 is no longer limited in the groove rail 131. Consequently, the plunger 110 is rotatable. The protruding wall 114 being no longer limited in the groove rail 131 means that the protruding wall 114 can leave the groove rail 131, for example, leave the fastening assembly 13, enter other branches on the wall of the through hole 133, or enter the fastening portion 132.

In an embodiment, one end of the slot, as the fastening portion 132, is open, and the other end is a closed end 132a. Therefore, after the plunger 110 is rotated and the protruding wall 114 is received in the receiving space of the slot, the lower closed end 132a abuts against the protruding wall 114, thus limiting the displacement of the plunger body 111.

Figures 1, 3A:
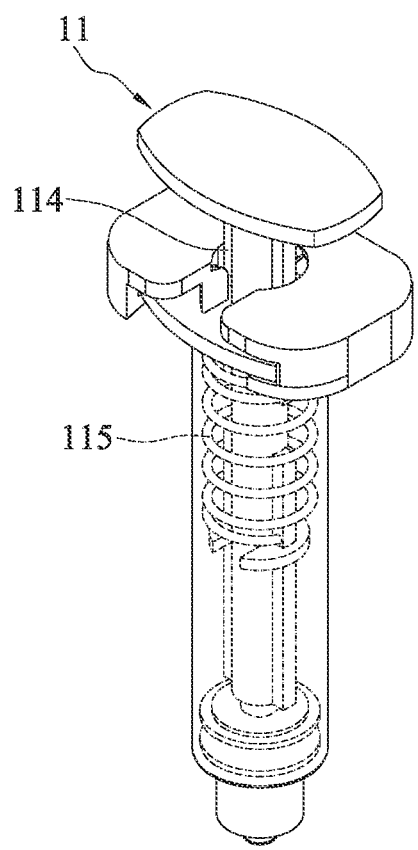
Figures 2, 3A:
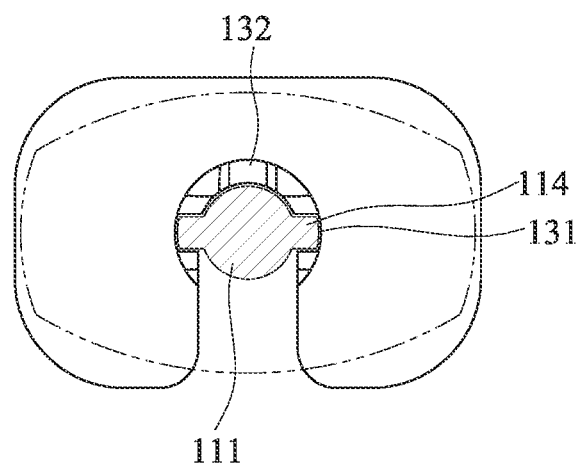

Referring to FIGS. 3A-1 and 3A-2, During sampling, by applying a force to the end plate 112, the plunger member 11 leaves the end wall of the injection hole, and the protruding wall 114 on the plunger body 111 is guided by the groove rail 131 to move. As such, the plunger member 11 moves along the axial direction of the syringe barrel 12 and gradually moves away from the syringe barrel 12. At the same time, the spring 115 disposed around the plunger body 111 is compressed due to reduced space between the piston 118 and the fastening assembly 13.

Figures 1, 3B:
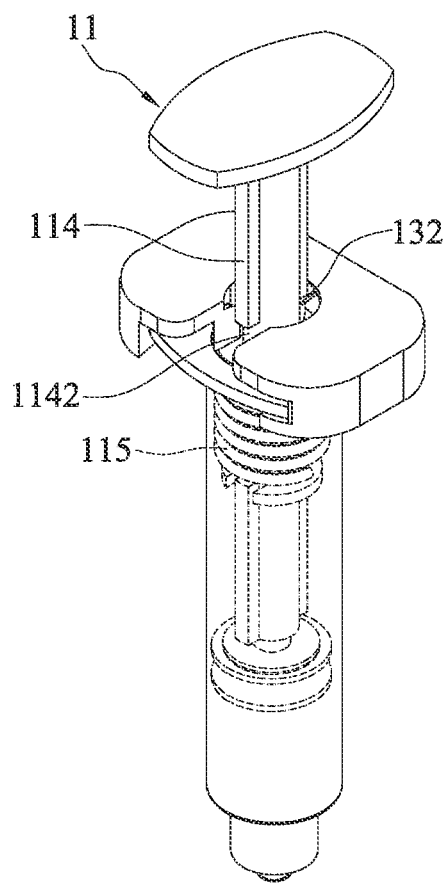
Figures 2, 3B:
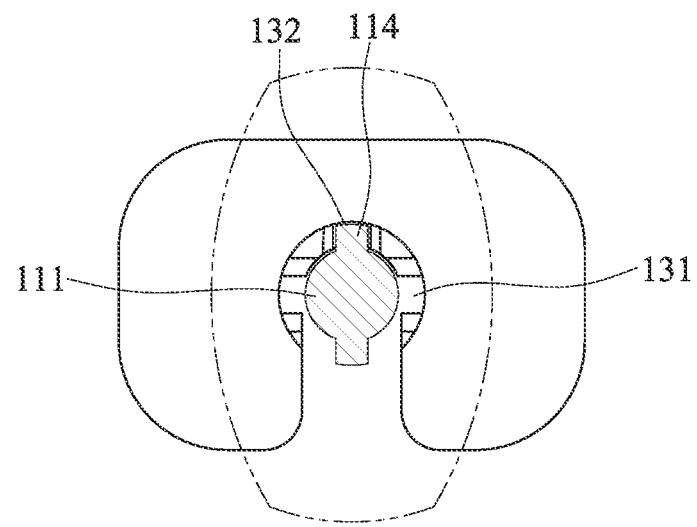

Then, referring to FIGS. 3B-1 and 3B-2, after sampling, the first recessed portion 1142 of the protruding wall 114 enters the groove rail 131. Since the space of the first recessed portion 1142 is greater than the limiting/guiding range of the groove rail 131, the plunger member 11 is no longer limited by the groove rail 131 and is rotatable. Therefore, by rotating the plunger member 11, the protruding wall 114 is moved to the fastening portion 132 (slot) and abuts against the closed end of the fastening portion 132 so as to be engaged with the fastening portion 132. At this point, the plunger member 11 is at a fixed position. In an embodiment, the plunger member 11 is rotated by 90 degrees. In other embodiments, the plunger member 11 can be rotated by any angle between 0 to 90 degrees.

During sample feeding, the plunger member 11 is rotated again to cause the protruding wall 114 to move back to the groove rail 131, and the plunger member 11 is automatically pushed into the syringe barrel 12 by an elastic restoring force of the spring 115 until the plunger member 11 abuts against the end wall of the injection hole of the syringe barrel 12.

In another embodiment, the plunger body 111 is further provided with a stop member 116, which is used to limit the disposing area of the spring 115 so as to suit different spring sizes or control the flow rate. In an embodiment, the disposing area of the spring 115 is from the piston 118/joining portion 113 to the fastening assembly 13. In another embodiment, the disposing area of the spring 115 is from the stop member 116 to the fastening assembly 13. The stop member 116 has a notch 117 and is disposed at a second recessed portion 1141 of the protruding wall 114 with the notch 117 engaged with the second recessed portion 1141.

In FIGS. 1 to 3B-1, two protruding walls 114 are provided and symmetrically arranged, and two groove rails 131 are provided. But in other embodiments, the number of the protruding walls 114 and the number of the groove rails 131 can be, but not limited to, one, three, four or more, respectively, as long as the number of the protruding walls 114 is not greater than the number of the groove rails 131. Further, the number of the fastening portion 132 can be, but not limited to, one, two, three, four or more.

A second aspect of the present disclosure is a semi-automatic sample feeding device, which has the above-described sampling device and a flow control device.

Figure 4A:
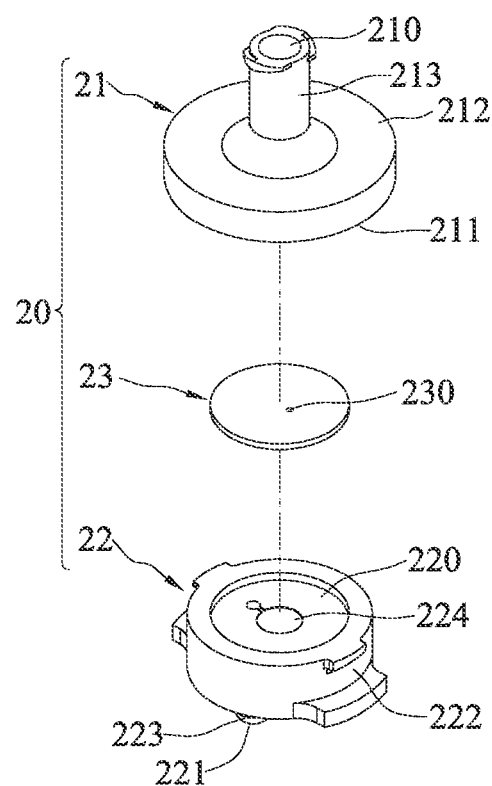
FIGS. 4A and 4B are schematic exploded and side cross-sectional views of a flow control device according to an embodiment of the present disclosure.
Figure 4B:
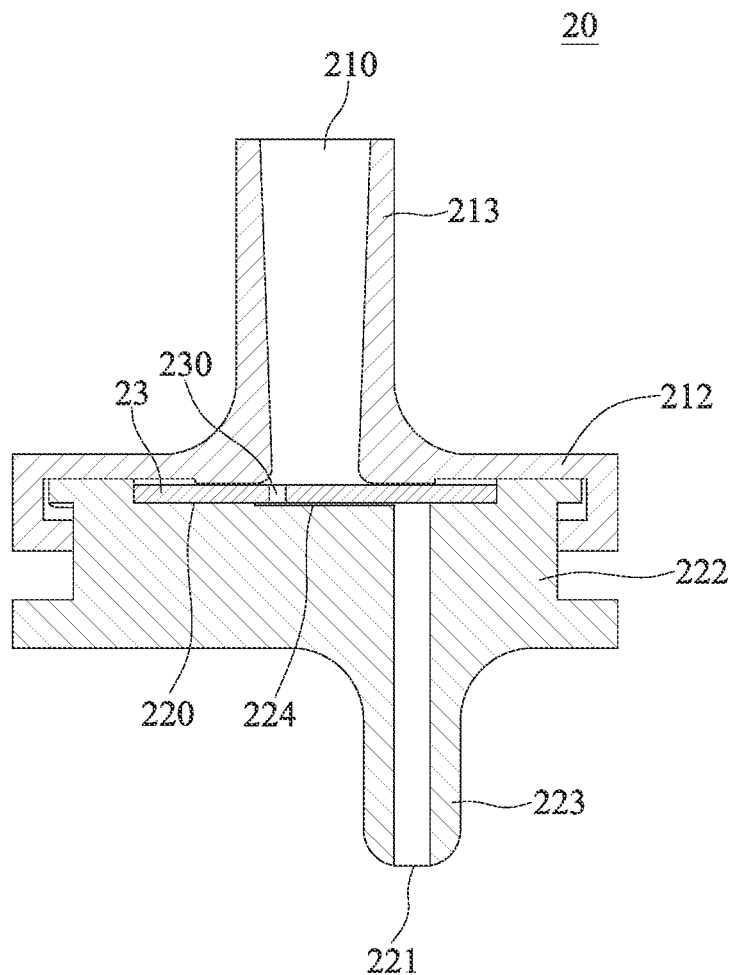

Referring to FIGS. 1, 4A and 4B, the semi-automatic sample feeding device has the sampling device 10 and the flow control device 20. After sampling of the sampling device 10, the sampling device 10 and the flow control device 20 are connected so as to push the sample into the flow control device 20.

Referring to FIGS. 4A and 4B, the flow control device 20 has a top member 21, a film 23 (e.g., a thin film) and a bottom member 22. The top member 21 and the bottom member 22 match one another and are closely joined together, and the film 23 is received and sealed inside the flow control device 20.

The top member 21 has an inflow channel 210, a bottom surface 211, a top member body 212, and a post portion 213, and the bottom member 22 has a discharge channel 221, a bottom member body 222, and a post portion 223. A film receiving space 220 is formed between the top member 21 and the bottom member 22 for receiving the film 23. In an embodiment, the film receiving space 220 is formed in the bottom member 22, and the film 23 is received in the film receiving space 220. The bottom member body 222 closely abuts against the bottom surface 211 of the top member 21 so as to avoid sample leakage.

The top member 21 and the bottom member 22 can be joined together by internal and external threads forming on them, respectively. For example, the top member body 212 has internal threads formed on an inner peripheral surface thereof, and the bottom member body 222 has external threads formed on an outer peripheral surface thereof and matching the internal threads. Therefore, the top member body 21 and the bottom member body 22 can be joined together through the matched internal and external threads. In other embodiments, the external threads can be formed on the top member body 212 and the internal threads can be formed on the bottom member body 222, or the top member body 21 and the bottom member body 22 can be joined together through a seal ring, an adhesive, a tape and so on.

The injection hole 121 of the syringe barrel 12 of the sampling device 10 is connected to the flow control device 20. In an embodiment, a front end of the syringe barrel 12 is inserted into the inflow channel 210 of the post portion 213 of the top member 21 so as to connect the injection hole 121 to the inflow channel 210, thereby allowing the sample to flow from the syringe barrel 12 to the flow control device 20. The post portion 213 has external threads formed on an outer peripheral surface thereof, and the front end of the syringe barrel 12 can have internal threads matching the external threads. As such, the post portion 213 can be closely connected to the syringe barrel 12 through the matched external and internal threads. In other embodiments, the post portion 213 can be connected to the syringe barrel 12 through a seal ring, an adhesive, a tape or the like. Alternatively, two ends of a hose can be connected to the front end of the syringe barrel 12 and the post portion 213 of the top member 21, respectively.

After the sampling device 10 is connected to the flow control device 20, the elastic restoring force provided by the spring 115 of the sampling device 10 can push the plunger member 11 so as to cause the sample to enter the flow control device 20. The sample flows through the channel of the post portion 213 into a space surrounded by the top member body 212 and the bottom member body 222 and contacts the film 23 first. At this point, the sample flow is blocked by the film 23, thereby generating a back pressure. The sample flow passes through a gap between the film and the film receiving space, and flows through a tube to a test paper device where the sample is captured by a test paper and reacts with the test paper. In the process, the back pressure can stably control the sample flow rate.

In the present disclosure, the inflow channel and the discharge channel of the flow control device can be vertically aligned and communicate with one another. In another embodiment, in order to improve the stable flow rate, the inflow channel and the discharge channel of the flow control device do not vertically communicate with one another. Specifically, the sample enters the inflow channel 210 and comes into contact with the film 23 so as to generate a back pressure, and thereafter, the sample flows to a buffer region 224 below the film 23 and then flows along a guide path to the discharge channel 221. As such, the sample is prevented from directly entering the discharge channel 221 after coming into contact with the film 23. "Not vertically communicate with one another" means that the inflow channel and the discharge channel communicate with the film receiving space in an unaligned manner.

On the other hand, the material and thickness of the film affect the back pressure. In an embodiment, the film is made of, but not limited to, polysiloxane (e.g., a polymer), such as polydimethylsiloxane (PDMS). The film has a thickness between 1.2 mm and 2.2 mm.

In other embodiments, the film can have a through hole. The sample can flow through the through hole to a lower test paper. In this way, the back pressure can also be controlled. The number of the through hole can be one or more. The through hole has a size between 0.5 mm and 3 mm.

A third aspect of the present disclosure is a test paper detection system, which has the above-described semi-automatic sample feeding device and the test paper device.

Figure 5A:
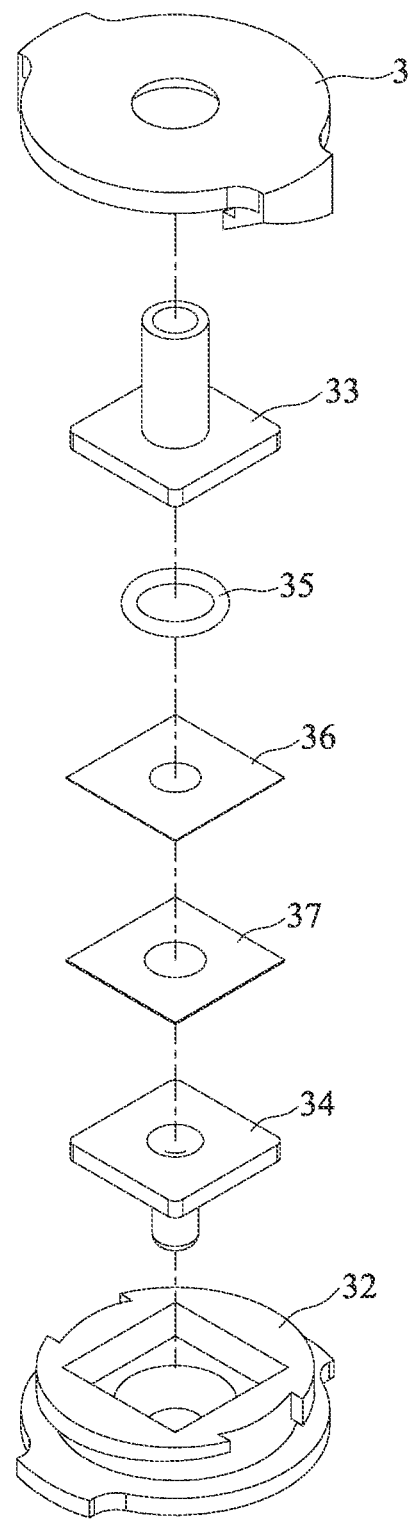
FIGS. 5A and 5B are schematic exploded and side cross-sectional views of a test paper device according to an embodiment of the present disclosure.
Figure 5B:
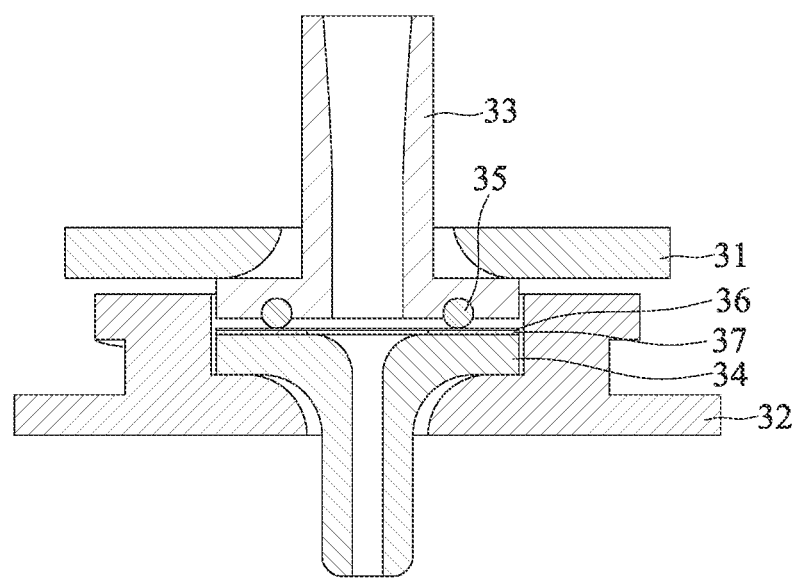

Referring to FIGS. 1, 5A and 5B, the test paper detection system 1 has the sampling device 10, the flow control device 20 and the test paper device 30. The sampling device 10 is connected to the flow control device 20, and the flow control device 20 is further connected to the test paper device 30. The sample is pushed into the test paper device 30 from the sampling device 10, and the flow rate is stabilized by the flow control device 20.

The test paper device has a top assembly, a test paper and a bottom assembly. The top assembly and the bottom assembly are closely joined together, and the test paper is sealed between the top assembly and the bottom assembly. Referring to FIGS. 5A and 5B, the test paper 36 is received and sealed in the test paper device. In an embodiment, the top assembly can have a top housing 31 and a top internal member 33, and the bottom assembly can have a bottom housing 32 and a bottom internal member 34. The top housing 31 is disposed around the top internal member 33, and the bottom housing 32 is disposed around the bottom internal member 34. The top internal member 33 has an inflow channel and the bottom internal member 34 has a discharge channel so as to allow inflow and discharge of the sample.

The top assembly and the bottom assembly can be joined in the same manner as the above-described top and bottom members of the flow control device, and the flow control device and the test paper device can be connected in the same manner as the above-described sampling device and the flow control device.

In an embodiment, both the top internal member 33 and the bottom internal member 34 have a platform surface on which the test paper 36 can be placed so as to be sandwiched between the top internal member 33 and the bottom internal member 34.

In another embodiment, in order to prevent the sample from leaking from a gap instead of properly contacting and reacting with the test paper, a seal ring 35 such as an O-ring can be disposed between the top internal member 33 and the test paper 36. In another embodiment, a carrier plate 37 is disposed between the bottom internal member 34 and the test paper 36 for carrying the test paper 36. The carrier plate 37 can support the test paper 36 so as to avoid deformation of the test paper under a sample flow pressure, thereby ensuring that the sample properly contacts and reacts with the test paper. Further, the carrier plate has pores. After contacting and reacting with the test paper, the sample can flow out of the carrier plate 37 through the pores. The carrier plate can be a cellulosic paper or other porous or permeable paper or film.

In other embodiments, the test paper 36 can be a test paper plate with a test paper. The area surrounded by the above-described seal ring is greater than the test paper so as to completely cover the test paper.

The test paper of the present disclosure can be, but not limited to, a fluorescent or colorimetric test paper. Further, one or more test papers can be provided. In addition, a plurality of test papers can be provided in a stack manner.

The above-described descriptions of the detailed embodiments are to illustrate the preferred implementation according to the present disclosure, and it is not to limit the scope of the present disclosure. Accordingly, all modifications and variations completed by those with ordinary skill in the art should fall within the scope of present disclosure defined by the appended claims.

What is claimed is:

1. A sampling device, comprising:
a syringe barrel having an injection hole and an opening opposite to one another, and a holding portion formed at an outer edge of the opening;
a plunger body axially disposed in the syringe barrel through the opening, wherein a protruding wall is formed in an axial direction of the plunger body, and a first break is formed in an extending direction of the protruding wall;
a spring disposed around the plunger body; and
a fastening assembly having a through hole allowing the plunger body to penetrate therethrough and an engaging structure communicating with the through hole, wherein the fastening assembly is engaged with the holding portion through the engaging structure, and a groove rail is formed on a wall of the through hole for receiving the protruding wall of the plunger body, and a fastening portion is formed on the wall of the through hole for limiting a displacement of the plunger body.

2. The sampling device of claim 1, wherein when the protruding wall moves along the axial direction of the syringe barrel in the groove rail for the plunger body to gradually move away from the syringe barrel, the spring is compressed synchronously.

3. The sampling device of claim 1, wherein in the axial direction of the plunger body, a length of the first break is greater than or equal to a length of the groove rail.

4. The sampling device of claim 1, wherein the fastening portion constructs a structure providing a receiving space in communication with the through hole such that when the first break of the plunger body enters the groove rail, the plunger body is rotatable to allow the protruding wall to be received in the receiving space.

5. The sampling device of claim 4, wherein the structure constructed by the fastening portion is a slot adjacent to the through hole.

6. The sampling device of claim 5, wherein the slot has a closed end and the protruding wall abuts against the closed end, thereby limiting the displacement of the plunger body.

7. The sampling device of claim 1, wherein the plunger body further has a stop member for limiting the spring between the stop member and the fastening assembly.

8. The sampling device of claim 7, wherein the protruding wall further has a second break for the stop member to be engageably disposed in the second break of the plunger body.

9. A semi-automatic sample feeding device, comprising the sampling device of claim 1 and a flow control device connected to the injection hole of the sampling device.

10. The semi-automatic sample feeding device of claim 9, wherein the flow control device comprises a top member, a film and a bottom member, and wherein the top member and the bottom member are joined together with a film receiving space formed therebetween for receiving the film.

11. The semi-automatic sample feeding device of claim 10, wherein the top member has an inflow channel and the bottom member has a discharge channel, and the inflow channel and the discharge channel communicate with the film receiving space in an unaligned manner.

12. The semi-automatic sample feeding device of claim 10, wherein the film has a through hole.

13. The semi-automatic sample feeding device of claim 10, wherein the film is made of a polysiloxane polymer.

14. The semi-automatic sample feeding device of claim 10, wherein the film has a thickness between 1.2 mm and 2.2 mm.

15. A test paper detection system comprising the semi-automatic sample feeding device of claim 9 and a test paper device connected to the discharge channel of the flow control device.

16. The test paper detection system of claim 15, wherein the test paper device comprises a top assembly, a test paper and a bottom assembly, and wherein the top assembly and the bottom assembly are joined together with the test paper sealed between the top assembly and the bottom assembly.

17. The test paper detection system of claim 16, wherein the top assembly comprises a top housing and a top internal member disposed in the top housing, and the bottom assembly comprises a bottom housing and a bottom internal member disposed in the bottom housing.

18. The test paper detection system of claim 16, wherein the test paper is a fluorescent or colorimetric test paper.

19. The test paper detection system of claim 18, wherein a plurality of the test papers are provided in a stack manner.

\* \* \* \* \*